United States Patent [19]

Houghton et al.

[11] Patent Number: 4,781,711
[45] Date of Patent: Nov. 1, 1988

[54] ABSORBENT ARTICLE HAVING MOISTURE INSENSITIVE RESILIENT SHAPING MEMBERS

[75] Inventors: Dawn I. Houghton, Fairfield; Nicholas A. Ahr, Cincinnati, both of Ohio

[73] Assignee: The Procter & Gamble Company, Cincinnati, Ohio

[21] Appl. No.: 93,075

[22] Filed: Aug. 28, 1987

Related U.S. Application Data

[63] Continuation of Ser. No. 794,820, Nov. 4, 1985, abandoned.

[51] Int. Cl.$^4$ .................. A61F 13/16; A61F 13/18; A61F 13/20
[52] U.S. Cl. .................. 604/378; 604/385.1; 604/367
[58] Field of Search ............... 604/368, 378, 358, 367, 604/385.1, 372, 376, 381, 382

[56] References Cited

U.S. PATENT DOCUMENTS

| | | | |
|---|---|---|---|
| 2,693,439 | 11/1954 | Blanchard et al. | 604/368 |
| 3,180,335 | 4/1965 | Duncan et al. | 604/378 |
| 3,343,543 | 9/1967 | Glassman | 604/385.1 |
| 3,364,931 | 1/1968 | Hirsch | 128/290 |
| 3,699,966 | 10/1972 | Chapuis | 604/378 |
| 3,814,100 | 6/1974 | Nystrand et al. | 128/287 |
| 3,863,637 | 2/1975 | MacDonald et al. | 128/287 |
| 3,865,111 | 2/1975 | Brooks | 604/378 |
| 3,865,112 | 2/1975 | Roeder | 128/290 R |
| 3,874,385 | 4/1975 | Gellert | 604/385.1 |
| 3,968,798 | 7/1976 | Hokanson | 604/368 |
| 3,995,640 | 12/1976 | Schaar | 604/378 |
| 4,029,101 | 6/1977 | Chesky et al. | 128/290 R |
| 4,212,302 | 7/1980 | Karami | 604/385.1 |
| 4,294,253 | 10/1981 | Friese | 604/385.1 |
| 4,410,324 | 10/1983 | Sabee | 604/368 |
| 4,413,996 | 11/1983 | Taylor | 604/382 |
| 4,501,586 | 2/1985 | Holtman | 604/385.1 |
| 4,505,705 | 3/1985 | Matthews et al. | 604/385.1 |
| 4,576,596 | 3/1986 | Jackson et al. | 604/385.1 |
| 4,731,070 | 3/1988 | Koci | 604/385.1 |
| 4,731,071 | 3/1988 | Pigneul | 604/385 R |

FOREIGN PATENT DOCUMENTS 2124907A 2/1984 United Kingdom .
85/02110 5/1985 World Int. Prop. O. .......... 604/368

Primary Examiner—C. Fred Rosenbaum
Assistant Examiner—Sharon Rose
Attorney, Agent, or Firm—Steven W. Miller; John M. Pollaro; Fredrick H. Braun

[57] ABSTRACT

The present invention provides a disposable absorbent article such as an incontinent pad that is both comfortable and suitable for absorbing and containing large volumes of body liquids rapidly without leakage, especially a subsequent gush of liquid. Such an absorbent article comprises a liquid pervious topsheet, a liquid impervious backsheet, a layered expandable absorbent core positioned between the topsheet and the backsheet, at least two resilient shaping members, an acquisition channel, a liquid acquisition zone and at least two liquid impervious shelves. The present invention also relates to an absorbent article provided with an expandable overwrap having an expansion means for allowing the overwrap to expand when the absorbent core swells when wetted. The resilient shaping members of the present invention provide an improved absorbent article design having raised side edges and an acquisition channel. The resilient shaping members are a compressible, conformable, resilient, and moisture insensitive batt of fibers so that the resilient shaping members will retain their shape even when wetted.

28 Claims, 2 Drawing Sheets

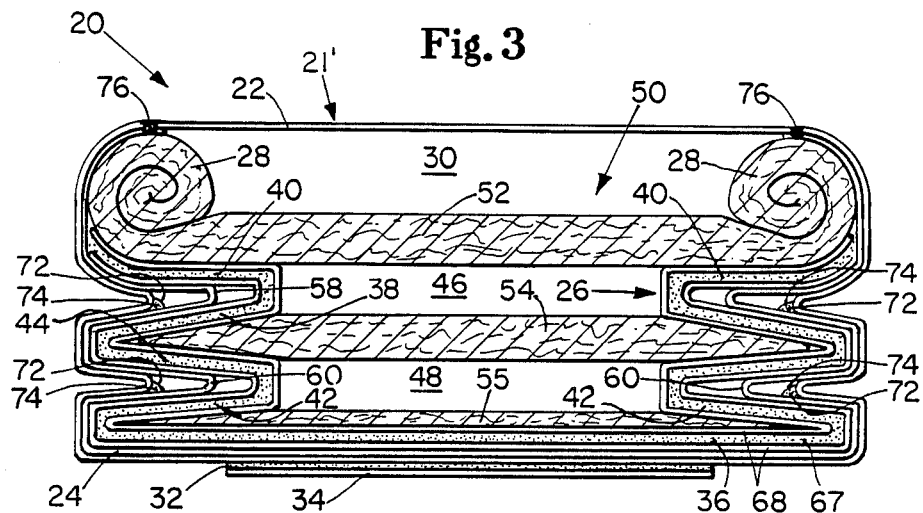
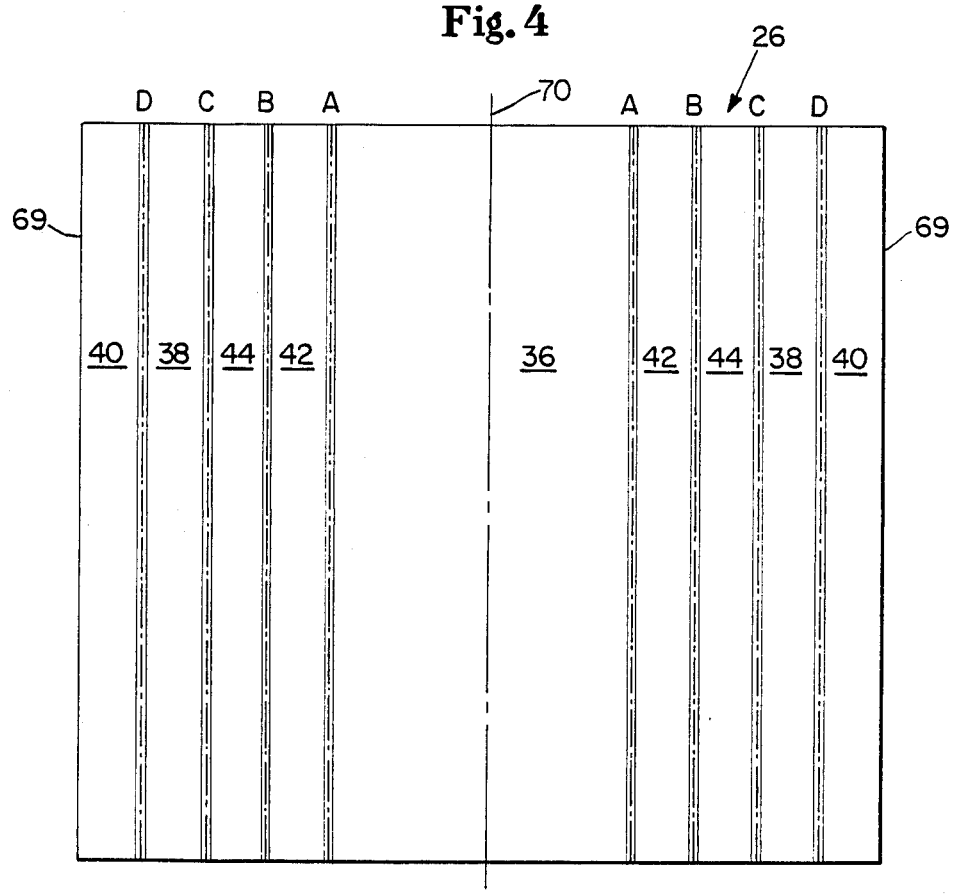

ABSORBENT ARTICLE HAVING MOISTURE INSENSITIVE RESILIENT SHAPING MEMBERS

This is a continuation of application Ser. No. 06/794,820, filed on Nov. 4, 1985, now abandoned.

FIELD OF THE INVENTION

The present invention relates to absorbent articles such as incontinent pads, and more particularly, to absorbent articles which are comfortable yet capable of rapidly accepting and containing large volumes of liquids.

BACKGROUND OF THE INVENTION

There is a growing awareness of the lack of satisfactory products designed for mobile persons with incontinent infirmities. While sanitary napkins, pantiliners, disposable brief and diapers are available for the mobile incontinent person, such products are not satisfactory from either a comfort or a protection standpoint. Catamenial products such as pantiliners and sanitary napkins are very comfortable to use. However, these products fail to achieve a satisfactory level of containment for high void levels of urine. While diapers and briefs meet the containment needs of the incontinent person, these products lack the comfort and discreteness available from sanitary napkins and pantiliners.

Thus, it is desirable to provide an absorbent article such as an incontinent pad that is comfortable and discrete, yet provides superior protection and containment. In order to achieve the goal of providing such an absorbent article, it is necessary that the absorbent article be capable of rapidly accepting and containing a large volume of liquid with a small surface area; rapidly distributing the liquid efficiently throughout the product; conforming to the body of the wearer; maintaining good body contact (i.e., the maintenance of the article in close proximity to and in conformity with the body of the wearer); and maintaining its integrity even when wetted so as to be effective to accept and contain a subsequent discharge or gush of liquid and to prevent rewet (i.e., recontact of liquids contained in the article with the skin of the wearer due to forces that squeeze the liquid out of the article).

One of the methods for enhancing the absorptivity of such products is to provide a void space or reservoir that is located near the top surface of the article. Examples of these type of products are disclosed in U.S. Pat. No. 3,364,931 issued Jan. 23, 1968 to W. F. Hirsch; U.S. Pat. No. 4,029,101 issued June 14, 1977 to Chesky et al., and U.S. Pat. No. 4,501,586 issued Feb. 26, 1985 to Holtman. Such articles, while providing some measure of increased ability to accept large volumes of liquid, are often incapable of both effectively accepting a subsequent discharge or gush of liquid and preventing rewet. This is due to the lack of integrity or form retention capacity of the materials after being wetted. Absorbent cores such as those formed of creped wadding or cellulosic fibers have a tendency to split, ball or lump when wetted. They thereby become relatively shapeless and non-form-sustaining. These elements also tend to flatten out and become compacted when subjected to forces. Because an absorbent article is subject to various forces during use, the article will tend to lose its shape when wetted. Thus, it will not conform to the body of the wearer resulting in discomfort for the wearer. In addition, the wetted and compressed absorbent core will have lost its ability to absorb a subsequent discharge or gush of liquid resulting in an increased likelihood of leakage and failure of the product. Further, because the void space or reservoir tends to lose its size and shape, not only is there a decreased ability to contain high volumes, but there is also an increased danger of rewet as the overwrap is no longer spaced away from the absorbent core.

Thus, there is a need to provide an absorbent article wherein the article will retain its shape after being wetted so as both to remain comfortable and to be able to rapidly absorb and contain a subsequent gush of liquid without increasing the likelihood of leakage or rewet. Accordingly, it would be advantageous to provide an absorbant article that is moisture insensitive without a loss in comfort or absorbent material would also be advantageous to provide an article having increased absorption and increased comfort.

Another method for increasing the absorbency of absorbent articles is to provide them with water-insoluble hydrogels. Water-insoluble hydrogels are polymeric materials which are capable of absorbing large quantities of liquids and which are further capable of retaining such absorbed liquids under moderate pressures. These absorption characteristics of water-insoluble hydrogels make such materials especially useful for incorporation into absorbent articles such as incontinent pads.

The effectiveness of liquid-absorbing hydrogel materials in disposable absorbent articles can be quite dependent upon the form, position and/or manner in which the hydrogel material is incorporated into the absorbent article. In some cases, for example, the effectiveness of hydrogel liquid absorption in absorbent articles can be adversely affected by a phenomenon called "gel blocking". The term gel blocking describes a situation that occurs when a hydrogel particle, film, fiber, composite, etc. is wetted. Upon wetting, the surface of the hydrogel material swells and inhibits liquid transmission to the interior of the absorbent material. Wetting of the interior subsequently takes place via a very slow diffusion process. In practical terms, this means that absorption of liquid by the article is much slower than discharge of liquid to be absorbed, and failure of the absorbent article may take place well before the hydrogel material in the absorbent article is fully saturated.

Thus, there is a continuing need to identify hydrogel-containing absorbent articles wherein the hydrogel material is especially effective and efficient in performing its intended function of holding discharged body liquids without interfering with the acquisition and distribution of body liquids by and within the article. Hydrogel materials are generally significantly more expensive than readily available absorbent fiber materials (e.g., cellulose fibers). Accordingly it would be advantageous to provide articles wherein either absorbent capacity of the hydrogel-containing article can be improved or wherein a given absorbent capacity of an article can be maintained while reducing the amount of relatively expensive hydrogel material used. It would also be advantageous to provide articles wherein the liquid-storing hydrogel material does not adversely affect the ability of the absorbent article to quickly acquire discharge body liquids.

In addition, because hydrogel material swells and expands upon being wetted, the hydrogel-containing absorbent core also must expand. Because the overwrap is generally firmly affixed around the absorbent article, the only space available for expansion of the absorbent core is within the interior of the absorbent article. This is especially imporant for incontinent pads or other absorbent articles that have a void space or reservoir within the article. The hydrogel-containing absorbent core will thus expand into the void spaces resulting in a loss of void space, i.e., acquisition area. In addition, if there is no void space within the absorbent core can expand, the core will be squeezed and compressed resulting in an increased danger of rewet. Therefore, there is a need to identify hydrogel-containing absorbent articles wherein the overwrap can expand as the hydrogel expands. Accordingly, it would be advantageous to provide articles wherein an expansion means allows the overwrap to continually adjust as the hydrogel expands. It would also be advantageous to provide articles wherein the manufactured size of the void spaces and channels are maintained during expansion of the article.

Therefore, it is an object of the present invention to provide an absorbent article which is able to rapidly accept and contain a large void of body liquids without leakage.

It is an additional object of the present invention to provide an absorbent article having improved comfort in both the wet and dry state for the wearer.

It is a further object of the present invention to provide an absorbent article having a resilient shaping member which is moisture insensitive so as to provide an acquisition channel to quickly accept and contain large voids of body liquid, and to prevent these liquids from passing back through the topsheet to rewet the wearer.

It is also an object of the present invention to provide an absorbent article having a liquid impervious shelf to more efficiently utilize the hydrogel material capacity of the absorbent core.

It is a further object of the present invention to provide an absorbent article having an overwrap and a releasing means so that when the hydrogel-containing absorbent core expands when wetted, the overwrap will expand maintaining the surface area of the article and at least maintaining and possibly increasing the volume of the liquid acquisiton zone during use.

These and other objects of the invention will be more readily apparent when considered and referenced to the following description and when taken in conjunction with the accompanying drawings.

SUMMARY OF THE INVENTION

The present invention provides a disposable absorbent article such as an incontinent pad that is both comfortable and suitable for absorbing and containing large volumes of body liquids rapidly without leakage, especially a subsequent gush of liquid. Such an absorbent article comprises a liquid pervious topsheet, a liquid impervious backsheet, a layered expandable absorbent core positioned between the topsheet and the backsheet, at least two resilient shaping members, an acquisition channel, a liquid acquisition zone and at least two liquid impervious shelves. The present invention also relates to an absorbent article provided with an expandable overwrap having an expansion means for allowing the overwrap to expand when the absorbent core swells when wetted.

The resilient shaping members of the present invention provide an improved absorbent article design having raised side edges and an acquisition channel. The resilient shaping members are a compressible, conformable, resilient, and moisture insensitive batt of fibers so that the resilient shaping members will retain their shape even when wetted.

The liquid impervious shelves comprise a multiplicity of shelf layers formed from a portion of the backsheet being folded. The liquid impervious shelves channel the flow of liquids toward the lower layers of the absorbent core and encourage use of the bottom and sides of the layers, thereby providing more efficient use of hydrogen materials. An anti-bunching bead may be placed on each liquid impervious shelf between the shelf layers to provide stability to the absorbent article.

The overwrap of the absorbent article is provided with an expansion means for permitting the overwrap to expand as the absorbent core swells when it is wetted. The expansion means is a releasable tack or other means that releases the overwrap when a slight shearing or peeling force or action is applied to the expansion means. Thus the swelling of the absorbent core is less likely to deform the shape of the pad or cause a loss of the absorptive capacity of the article, especially for subsequent gushes of liquids.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substatially identical elements, and in which:

FIG. 3 is a fragmentary sectional view of an alternative embodiment of the present invention.

FIG. 4 is a plan view of the absorbent core of the present invention prior to folding the absorbent core to its preferred shape.

DETAILED DESCRIPTION OF THE INVENTION

Figure 1:
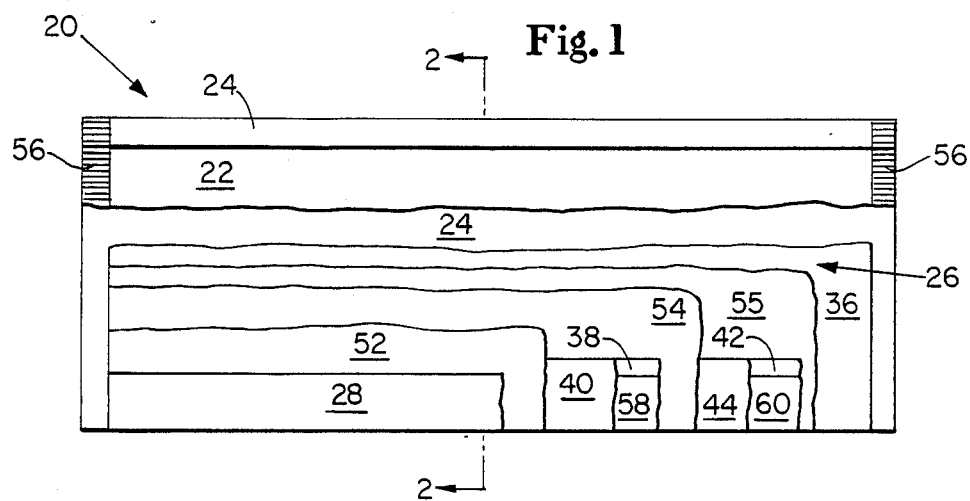
FIG. 1 is a plan view of an incontinent pad embodiment of the present invention having portions cut away to reveal the underlying structure.

As used herein, the term "disposable absorbent article" refers to articles which absorb and contain body liquids and more specifically refers to articles which are placed against or in proximity to the body of the wearer to absorb and contain the various liquids discharged from the body, and which are intended to be discarded after a single use (i.e., they are not intended to be laundered or otherwise restored and reused). A preferred embodiment of the disposable absorbent article of the present invention, incontinent pad 20, is shown in FIG. 1 and in cross-sectional view in FIG. 2. As used herein, the term "incontinent persons" by adhesively attaching the pad directly to the crotch region of the wearer's undergarment. It should be understood, however, that the present invention is also applicable to other disposable absorbent articles such as incontinent briefs, diapers, sanitary napkins, and the like.

Figure 2:
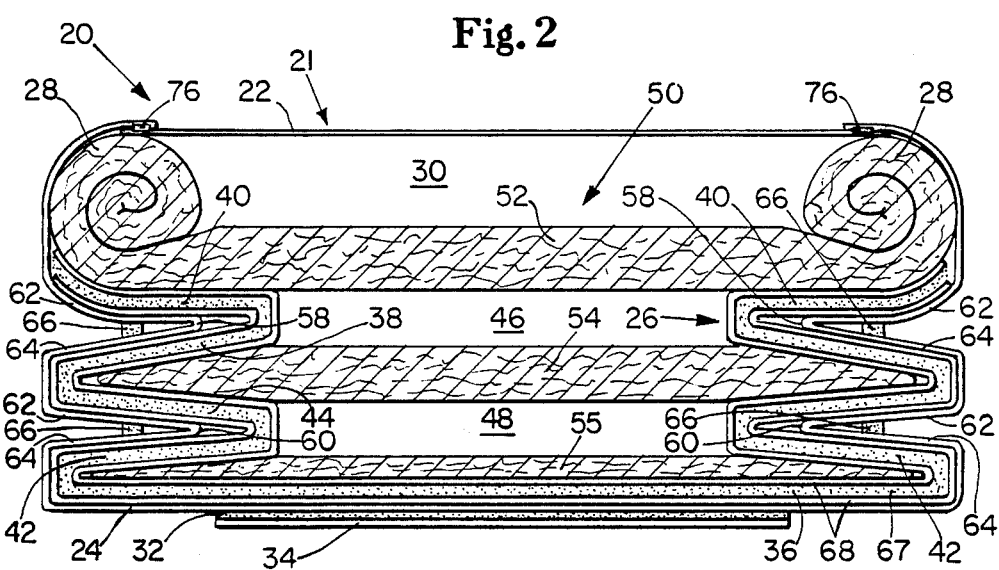
FIG. 2 is a fragmentary sectional view of the present invention taken along section line 2—2 of FIG. 1.

FIG. 1 is a plan view of the incontinent pad 20 of the present invention with portions of the structure being cut away to more clearly show the construction of the incontinent pad 20 and with the portion of the incontinent pad 20 which contacts the wearer facing the viewer. The incontinent pad 20 comprises an overwrap 21 exemplified by a liquid pervious topsheet 22 and a liquid impervious backsheet 24. Positioned between the topsheet 22 and the backsheet 24 is an absorbent core 26. As shown in FIG. 2, the absorbent core 26 preferably comprises two or more distinct layers. At least two resilient shaping members 28 are positioned between the absorbent core 26 and the topsheet 22. As shown in FIG. 2, the resilient shaping members 28 are disposed one at each side of the incontinent pad 20 in a spaced relation to each other. An acquisition channel 30 is positioned between the topsheet 22 and the absorbent core 26 and is longitudinally bounded by at least the spaced apart resilient shaping members 28. As shown in FIG. 2, the acquisition channel 30 is preferably positioned directly below the topsheet 22 to provide and incontinent pad 20 that will rapidly accept large void volumes of liquid. The liquid impervious backsheet 24 preferably extends along the bottom and sides of the incontinent pad 20 and covers a portion of each of the resilient shaping members 28 so as to provide a liquid impervious barrier to contain liquids within the incontinent pad 20. The backsheet 24 is preferably associated with the topsheet 22 adjacent each of the resilient shaping members 28; the topsheet 22 thereby covering the acquisition channel 30 and at least a portion of each resilient shaping member 28. Secured along the bottom of the incontinent pad 20 on the backsheet 24 is an adhesive attachment means 32 that is covered by a removable release liner 34.

As shown in FIGS. 1 and 2, the absorbent core 26 is preferably a unified web of material arranged in a multiplicity of layers; the layers being formed by longitudinally extending folds in the web. The absorbent core 26 thereby has a number of layers positioned in each side of the incontinent pad 20 and a central void space or channel to allow liquids to rapidly be acquired by the pad. As shown in FIG. 2, the absorbent core 26 preferably has a base layer 36 positioned adjacent the backsheet 24, at least two first support layers 38, at least two first side margin layers 40, at least two second support layers 42, and at least two second side margin layers 44. Each set of support layers and the side margin layers are disposed in a spaced relation to each other. Each of the sets of side margin layers should be spaced apart so as not to block the rapid inflow of liquids within the incontinent pad 20 and the absorbent core 26. The absorbent core 26 thus has a first central channel 46 longitudinally bounded by the first side margin layers 40 and the first support layers 38 and a second central channel 48 longitudinally bounded by the second side margin layers 44 and the second support layers 42.

Because hydrogel materials absorb liquids slowly and expand or swell upon being wetted, the incontinent pad 20 must be provided with void space for rapid liquid acquisition and storage. This void space is generally referred to as a liquid acquisition zone 50. The volume of the liquid acquisition zone 50 must, therefore, be at least as large as the liquid volume the incontinent pad 20 is expected to accept, absorb and contain. As shown in FIG. 2, the liquid acquisition zone 50 comprises at least the resilient shaping members 28 and the acquisition channel 30. When the absorbent core 26 is a multilayered structure, the liquid acquisition zone 50 accidentally comprises the first centeral channel 46 and the second central channel 48 of the absorbent core 26. Additionally, in order to provide additional void space to accept and contain liquids, and to provide more rapid distribution of liquids throughout the pad, the incontinent pad 20 and the liquid acquisition zone 50 may additionally comprise a first liquid distribution layer 52, a second liquid distribution layer 54 and a third liquid distribution layer 55.

As illustrated in FIG. 1, the incontinent pad 20 is an elongate absorbent article intended to be maintained in the crotch region of the wearer to accept and absorb discharged liquids. The embodiment of the incontinent pad 20 illustrated in FIG. 1 has generally straight longitudinal sides and ends. However, any convenient design known to those skilled in the art can be used in the practice of the invention. The overwrap 21 such as the topsheet 22 and the backsheet 24 are shown in FIG. 1 to extend beyond the ends of the absorbent core 26, the topsheet 22 and the backsheet 24 being sealed along the ends by a seal 56.

FIG. 2 shows a preferred embodiment of the incontinent pad 20 in which the backsheet 24 extend around the bottom and the sides of the incontinent pad 20. On each side of the incontinent pad 20, the backsheet 24 has mutliple shelf layers formed by inwardly longitudinally extending folds of the backsheet 24. As shown in FIG. 2, there is at least two folds on each side of the incontinent pad 20, the folds defining a first liquid impervious shelf 58 and a second liquid impervious shelf 60, each shelf having at least a first shelf layer 62 and a second shelf layer 64. Each first shelf layer 62 is shown in FIG. 2 to be releasably secured to each second shelf layer 64 by an anti-bunching bead 66.

In FIG. 2 the overwrap 21 is shown in two sections, topsheet 22 and backsheet 24, rather than as a single section because of the ease of constructing the incontinent pad 20 when the overwrap is in two parts. It is to be understood that the precise number of sections joined to form the overwrap 21 is immaterial. In fact, an overwrap 21 constructed of a single section of material is illustrated and discussed as an alternative embodiment.

The topsheet 22 is the element of the incontinent pad 20 that is placed in close proximity to the skin of wearer. The topsheet 22 is compliant, soft feeling and non-irritating to the wearer's skin. Further, the topsheet 22 is liquid pervious permitting liquids to readily penetrate through its thickness. In general, porous materials used as topsheets for disposable diapers or as coverings for conventional sanitary napkins can be used in the present invention. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from the liquids in the absorbent core 26.

A particularly preferred topsheet 22 comprises staple length polypropylene fibers having a denier of about 1.5, such as Hercules Type 151 polypropylene marketed by Hercules, Inc. of Wilmington, Del. As used herein, the term "staple length fibers" refers to those fibers having a length of at least about 15.9 mm (0.625 inches).

There are a number of manufacturing techniques which may be used to manufacture the topsheet 22. For example, the topsheet 22 may be woven, non-woven, spunbonded, carded, or the like. A preferred topsheet 22 is carded, and thermally bonded by means well known to those skilled in the fabric arts. Preferably, the topsheet 22 has a weight from about 15 to about 25 grams per square meter, a minimum dry tensile strength of at least about 400 grams per centimeter in the machine direction and a wet tensile strength of at least about 55 grams per centimeter in the cross-machine direction.

In preferred embodiments of the present invention, the outer surface of the topsheet 22 is treated with a surfactant. Treating the outer surface of the topsheet 22 with surfactant renders such surface more hydrophilic which results in liquid penetrating the topsheet 22 faster than if the surface were not treated. This diminishes the likelihood that liquids will flow off the topsheet 22, which results in clothing and body soiling, rather than being absorbed by the absorbent core 26. It is preferred that the surfactant be substantially evenly and completely distributed throughout the outer surface of the topsheet 22. This can be accomplished by any of the common techniques well known to those skilled in the art. For example, the surfactant can be applied to the topsheet 22 by spraying, by padding or by the use of transfer rolls.

The backsheet 24 is impervious to liquids and is preferably manufactured from a thin plastic film, although other flexible liquid impervious materials may also be used. The backsheet 24 prevents body liquids absorbed and contained in the absorbent core 26 from wetting articles which contact the incontinent pad 20 such as undergarments. Preferably, the backsheet 24 is a polyethylene film having a thickness of from about 0.012 mm (0.5 mil) to about 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as film number 8020. The backsheet 24 is preferably embossed and/or matte finished to provide a more clothlike appearance. Further, the backsheet 24 may permit vapors to escape from the absorbent core 26 while still preventing liquids from passing through the backsheet 24.

The size of the backsheet 24 is dictated by the size of the absorbent core 26 and the exact design selected. In a preferred embodiment, the backsheet 24 extends beyond each of the sides of the base layer 36 a distance of about 8.25 cm (3.25 inches) to about 15.25 cm (6 inches) to extend around at least the bottom and the sides of the incontinent pad 20 and also preferably a portion of each of the resilient shaping members 28. In addition, the backsheet 24 extends beyond the ends of the absorbent core 26 and is sealed to at least the topsheet 22 by a seal 56.

The topsheet 22 and the backsheet 24 are associated together in any suitable manner. As used herein, the term "associated" encompasses configurations whereby the topsheet 22 is directly joined to the backsheet 24 by affixing the topsheet directly to the backsheet 24, and configurations whereby the topsheet 22 is indirectly joined to the backsheet 24 by affixing the topsheet 22 to intermediate members which in turn are affixed to the backsheet 24. In a preferred embodiment, the topsheet 22 and the backsheet 24 are joined directly to each other adjacent the resilient shaping members 28 by adhesive attachment means 76 as are well known in the art.

The absorbent core 26 may be any means which is compressible, conformable, non-irritating to the wearer's skin, and capable of absorbing and retaining liquids. The absorbent core 26 may be formed from a wide variety of liquid absorbent materials commonly used in disposable diapers and other absorbent articles. Examples of suitable absorbent materials include comminuted wood pulp which is generally referred to as airfelt, creped cellulose wadding, absorbent foams, absorbent sponges, textile fibers, or any equivalent material or combination of materials. The total absorbent capacity of the absorbent core 26 should, however, be compatible with the design liquid loading in the intended use of the incontinent pad 20. Further, the size and absorbent capacity of the absorbent core 26 may be varied to accommodate different wearers.

Preferably, the absorbent core 26 consists essentially of a substantially uniform combination of hydrophilic fiber material and particular amounts of discrete particles of substantially water-insoluble, liquid-absorbing hydrogel material. Various types of hydrophilic fiber material as disclosed above can be used. Particularly preferred fibers include cellulose fibers, rayon, hydrophilized hydrophobic fibers such as sufactant-treated or silica treated thermoplastic fibers and polyester fibers. Most preferred materials are cellulose fibers, especially wood pulp fibers and wood pulp tissue.

In addition to the hydrophilic fiber material, the absorbent core 26 also preferably contains discrete particles of substantially water-insoluble hydrogel material. Such hydrogel materials are inorganic or organic compounds capable of absorbing liquids and retaining them under moderate pressures.

Suitable hydrogels can be inoragnic materials such as silica gels or organic compounds such as cross-linked polymers. Cross-linking may be covalent, ionic, van der Waals, or hydrogen bonding. Examples of hydrogel polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in Assarsson et al., U.S. Pat. No. 3,901,236, issued Aug. 26, 1975, which is herein incorporated by reference. Particularly preferred hydrogel polymers for use in the absorbent core 26 are hydrolyzed acrylonitrile grafted starch, acrylic acid grafted starch, polyacrylates, and isobutylene maleic anhydride copolymers, or mixtures thereof.

Processes for preparing hydrogels are disclosed in Mesuda et al., U.S. Pat. No. 4,076,663, issued Feb. 28, 1978; Tsubakimoto et al., U.S. Pat. No. 4,286,082, issued Aug. 25, 1981; and further in U.S. Pat. Nos. 3,734,876, 3,661,815, 3,760,731, 3,664,343, 3,783,871, the disclosures of which are all incorporated herein by reference.

Hydrogel material found in the absorbent core 26 herein is used in the form of discrete particles. Hydrogel particles can be of any desired shape, e.g., spherical or semi-spherical, cubic, rod-like, polyhedral, etc. Shapes having a large greatest dimension/smallest dimension ratio, like noodles, flakes and fibers, are also contemplated for use herein. Conglomerates of hydrogel particles may also be used.

In a particularly preferred embodiment of the present invention, the absorbent core 26 will comprise an intimate mixture of hydrophilic fiber material and hydrogel particles with the hydrogel particles preferably being substantially uniformly distributed throughout a hydrophilic fiber matrix.

The substantially uniform combination of hydrophilic fiber material and hydrogel particles used as the absorbent core 26 preferably comprises a laminate of dispersed hydrogel particles, generally shown as 67 interposed between layers of hydrophilic fiber material, generally shown as 68, such as tissue paper.

Alternatively, the absorbent core 26 can be formed by air-laying a dry mixture of hydrophilic fibers and hydrogel particles and densifying the resulting web. Such a procedure is described more fully in Proctor & Gamble; European Patent Publication No. EP-A-122,042; published Oct. 17, 1984, incorporated herein by reference. As indicated in this reference, the webs formed by this procedure for use as the absorbent core 26 will preferably comprise substantially unbonded fibers and will preferably have a moisture content of 10% or less.

The absorbent core 26 can be of any desired shape consistent with comfortable fit including for example, a circular, rectangular, trapezoidal, oblong, hourglass, dog bone or oval shape. Preferably, however, the absorbent core 26 will comprise a multi-layered construction. It should be understood for purposes of this invention that the term "layers" does not necessarily limit the invention to single layers or sheets of material. Thus, each of the layers may actually comprise laminates or combinations of several sheets or webs of the requisite type of materials as hereinafter described. Thus as used herein, the term "layer" includes the terms "layers" and "layered". Most preferably, the absorbent core 26 is a unified web arranged in a multiplicity of core layes, the core layers being formed by longitudinally extending folds in the web, the folds alternating in a zig-zag sequence in each side of the incontinent pad 20.

As shown in FIG. 4, the absorbent core 26 is preferably a square web of about 20 cm (8 inches) × 20 cm (8 inches) that is folded in a zig-zag sequence. In accordance with this folding sequence, each of the side edges 69 of the unified web of the absorbent core 26 is folded inwardly toward the longitudinal centerline 70 of the absorbent core 26 along a longitudinal fold line "A" located inwardly from the respective side edge of the absorbent core by about 6.4 cm (2.5 inches) of the absorbent core width, to define the second support layer 42. The side edges 69 are further folded outwardly from the pad centerline 70 along a second longitudinal fold line "B" spaced outwardly from the fold line "A" by about 1.6 cm (0.625 inches) to define a second side margin layer 44 overlying the second support layer 42. Still further, the side edges 69 are folded inwardly in the same direction as the first fold along a third longitudinal fold line "C" spaced outwardly from the fold line "B" by about 1.6 cm (0.625 inches) to define a first support layer 38 that overlies the second side margin layer 44. Even further, each of the side edges 69 is further folded outwardly from the centerline 70 along a fourth longitudinal fold line "D" spaced outwardly from the fold line "C" by about 1.6 cm (0.625 inches) to define a first side margin layer 40 overlying the first support layer 38.

An absorbent core 26 having multiple core layes as formed above offers several advantages. There are multiple surface areas available to absorb and contain large volumes of liquids. Because hydrogel materials tend to swell and inhibit liquid transmission to the interior of the absorbent material, it is desirable to provide as large a surface area as possible to initially contact acquired liquids. In the above arrangement of the absorbent core 26, most of the surface area available, in the layers are fully utilized. For example, the liquid impervious shelves transport some liquid to the "outside" surfaces of the side margin layers.

In addition to the increased surface area available this absorbent core 26 design allows free liquid to pass to lower layers of the absorbent core 26, especially the base layer 36. As shown in FIG. 2, the first side margin layers 40 and the second side margin layers are disposed in a spaced relation to each other. Therefore, the absorbent core 26 has a first central channel 46 and a second central channel that are longitudinaly bounded by the first side margin layers 40 and the first support layers 38 and the second side margin layers 44 and the second support layers 42, respectively. In order to insure that the channels will not be mechanically blocked by the swelled hydrogel-containing layers, the width of the central channels are critical. The transverse width of each of the central channels must be at least about one-sixth of the total transverse width of the incontinent pad 20, preferably being about one-half and most preferably about two-thirds of the total transverse width of the incontinent pad 20.

The absorbent core 26, and more particularly the base layer 36, is positioned between the topsheet 22 and the backsheet 24 and is preferably attached to the backsheet 24 by attachment means (not shown) such as those well known in the art. For example, the absorbent core 26 may be secured to the backsheet 24 by a uniform continuous layer of adhesive, a patterned layer of adhesive, or an array of separate lines or spots of adhesive. An adhesive which has been found to be satisfactory is manufactured by Eastman Chemical Products of Kingsport, Tenn. and marketed under the tradename Eastobond A-3.

The resilient shaping members 28 provide an improved incontinent pad design having raised side edges and an acquisition channel 30. The raised side edges are pressed up against the skin area around the perineal area by the wearer's undergarment thereby forming a gasketing effect leading to close body contact between the wearer and the incontinent pad 20. Liquid is thereby directed toward the middle of the incontinent pad 20 into the liquid acquisition zone 50 and the acquisition channel 30. In addition, because of the properties of the resilient shaping members 28 in retaining their shape and acquisition characteristics even when wet, the incontinent pad 20 is capable of acquiring a subsequent gush of liquid without increased likelihood of leakage. Because of its physical properties, the resilient shaping members 28 also enhance the comfort perceived by the wearer. The resilient shaping members 28 also serve as a reservoir in the liquid acquisition zone 50 for initially containing rapidly voided body liquids.

The resilient shaping members 28 are preferably disposed between the topsheet 22 and the absorbent core 26 in order to obtain the desired properties discussed above. While wicking layers or other materials may be placed between the topsheet 22 and the resilient shaping members 28, such an embodiment is not preferred. In addition, liquid distribution layers may be placed between the resilient shaping members 28 and the absorbent core 26. Preferably as shown in FIG. 2, the resilient shaping members and the first liquid distribution layer 52 are integrally formed from the same web of material, although the resilient shaping members 28 may also be separate elements from each other and/or the first liquid distribution layer 52.

The resilient shaping members 28 of the present invention may be formed in a number of ways. As is shown in FIG. 2, the material forming the resilient shaping members 28 may be inwardly rolled to bound an acquisition channel 30 that is wider at the top and at the bottom than it is in the middle. Alternatively, the material may be zig-zag folded, or a number of layers of material may be laid on top of each other to provide a resilient shaping member 28 of sufficient height. The height of the resilient shaping members 28 is critical to the size of the acquisition channel 30 bounded by the resilient shaping members 28. (Height being defined as the dimension measured from the lowest point to the uppermost point in the manufactured condition; i.e., the maximum thickness of the resilient shaping member 28.) If the resilient shaping members 28 are of insufficient height, the topsheet 22 will tend to bow and touch the lower layers of the incontinent pad 20, thereby resulting in a large amount of the volume of the acquisition channel 30 being lost. Therefore, it is preferably that the resilient shaping members 28 have a height in an uncompressed state of at least about 0.5 cm, and more preferably from about 1.0 cm to about 2.0 cm. As shown in FIG. 2, the resilient shaping members 28 have a height of about 1.5 cm.

To allow liquids to rapidly flow to the lower portions of the incontinent pad 20, the resilient shaping members 28 must be in a spaced relation to each other. As shown in FIGS. 1 and 2, the resilient shaping members 28 are in a longitudinal spaced relation to each other to bound a longitudinally extending acquisition channel 30. (A longitudinal spaced relation is defined as placing the elements lengthwise along the side of the pad so that there is a transverse width dimension separating the elements.) While the resilient shaping members 28 may be arranted in a number of different ways, a longitudinal spacing arrangement is preferred.

In order to provide an incontinent pad 20 capable of being both comfortable and protective, the resilient shaping members 28 should be compressible, conformable, and resilinet. That is to say, the resilient shaping members 28 must possess such physical properties so that forces applied to them by the action of the wearer will readily cause them to bend, to compress and to conform to a space available for them as the incontinent pad 20 is held adjacent the wearer's body. The resilient shaping members 28 must be resilient so that each must, without the application of external forces, return to essentially its original size and shape after the forming forces are removed. Preferably, the material used in manufacturing the resilient shaping members 28 possesses such resilience that it will recover at least about 80% of its original volume after it is compressed to about 20% of its original volume when the compressing forces are removed. Most preferably, the material 28 will recover at least about 90% of its original volume after it is compressed to about 50% of its original volume when the compressing forces are removed.

Because the incontinent pad 20 is designed to retain its shape during use, the resilient shaping members 28 must also be essentially unaffected by the presence of liquids such as urine; that is to say, the resilient shaping members 28 must possess a high degree of wet resiliency. The resiliency shaping members 28 must retain sufficient inherent resiliency, even when wet, to impart to the element sufficient elasticity to resist close parking of the fibers thereof and the retention of the characteristics of the springy three dimensional structure during use so that the incontinent pad 20 will retain its shape during subsequent gushes. Certain materials and fibers, such as rayon or cellulose fibers have a high degree of resiliency in the dry state, but are essentially non-resilient when wetted. Such materials and fibers are, in general, not useful in the present invention as resilient shaping members 28. The term "moisture insensitive" is used herein to describe materials and fibers whose resiliency is relatively unaffected by the presence of moisture.

Preferably the resilient shaping members 28 comprise a mass or batt of fibers. While the resilient shaping members 28 can comprise other materials, such as a synthetic foam material, such materials are less preferred than a fibrous batt. The batt of fibers is preferably formed of hydrophobic fibers of a synthetic material because these types of materials exhibit aninherent dry and wet resilience. Other materials may also be used as long as the fibers exhibit dry and wet resilience. For example, fibers that are bonded together at their points of intersection usually exhibit the necessary wet and dry resilience. The resiliency of fibers can be described by the initial modulus of the fibers. Initial modulus can be measured according to A.S.T.M. Standard Method D3822 (Standard Test Method for Textile Properties of Single Textile Fibers) which method is incorporated herein by reference. Fibers are said to be moisture insensitive when their initial modulus in the presence of moisture is at least about 90% of the initial dry state modulus.

Synthetic fibers useful in the present invention include those made of cellulose acetate, polyvinyl chloride, polyvinylidene chloride, acrylic resins, polyvinyl acetates, non-soluable polyvinyl alcohols, polyethylenes, polypropylenes, polyamides, and preferably, polyesters. Preferred are polyester fibers having a denier of from about 1 to about 15 and a length of from about 2 to about 8 centimeters. As indicated herein, the resiliency of the resilient shaping members 28 can frequently be enhanced if the fibers are bonded together at their points of contact. Thermal bonding can be used or adhesives, such as latex adhesives, can be used to bond the synthetic fibers one to another. Other examples of suitable batts of fibers useful in the present invention are found in U.S. Pat. No. 4,475,911 issued to Gellert on Oct. 9, 1984; U.S. Pat. No. 3,029,817 issued to Harwood et al., on Apr. 17, 1962; and U.S. Pat. No. 3,371,667 issued to Morse on Mar. 5, 1968, all of which are incorporated herein by reference.

Preferably, because the hydrogel-containing absorbent core 26 requires sufficient void volume to rapidly contain large quantities of liquids, it is desirable that the resilient shaping members 28 be able to contain practical quantities of liquids. The resilient shaping members 28 should, therefore, be manufactured of a material of relatively low density so that each resilient shaping member 28 has sufficient void volume in the interstices or capillaries between fibers to contain practical quantities of urine. A low density material also helps to insure that the resilient shaping members 28 are readily deformable under the influence of the wearer's body thereby exhibiting comfort attributes. Preferably, the density of the resilient material is from about 0.01 to about 0.5 grams per cubic centimeter.

Since the fibers are preferably hydrophobic and will not absorb liquids into their interiors, the surfaces of the fibers are also hydrophobic. Therefore, in order for the interstices of the batt of fibers to more easily contain sufficient quantities of liquids, the surfaces of the fibers can be hydrophilic. More generally, the resilient shaping members 28 can comprise a material having interstices or capillaries which are wetted by the liquids in question. Urine and other body liquids are primarily aqueous solutions and suspensions; surfaces which are wetted by these liquids can be broadly described as hydrophilic. As used in this specification, the term "hydrophilic", describes surfaces which are wetted by the liquid in question.

The state of the art respecting wetting of materials allows definition of hydrophilicity (and wetting) in terms of contact angles and the surface tensions of the liquids and solids involved. This is discussed in detail in American Chemical Society publication entitled, Contact Angle, Wetability, and Adhesion, edited by Robert F. Gould, any copyrighted in 1964, which publication is incorporated herein by reference. The surface is said to be wetted by a liquid either when the contact angle between the liquid and the surface is less than 90° or when the liquid will tend to spread spontaneously across the surface; both conditions normally coexist.

The materials used in the resilient shaping members 28 can achieve hydrophilicity by any convenient means. For example, the material itself can be intrinsically hydrophilic, although as discussed herein, this circumstance is relatively rare for materials useful in the resilient shaping members 28. The surfaces of the resilient shaping members 28 can be rendered hydrophilic by treatment with a surfactant, such as a non-ionic or anionic surfactant, as by spraying the material with a surfactant or dipping the material into the surfactant. By treating the surfaces of the fibers with a surfactant, only the surfaces of the fibers exhibit hydrophilic characteristics while the fiber itself remains hydrophobic.

Suitable surfactants include non-ionic surfactants such as Brij 76 manufactured by ICI Americas, Inc. of Wilmington, Del. and the various materials sold under the Pegosperse trademark by Glyco Chemicals, Inc. of Greenwich, Conn. Anionic surfactants can also be used. Surfactants are applied to the fibers at a level of from about 0.2 to about 1 gram per square meter of material.

Synthetic foams useful as a resilient shaping member 28 include polyester foam materials such as those described by Des Marais in U.S. Pat. No. 4,110,276 issued Aug. 29, 1978 and incorporated herein by reference, polyurethane foams, styrene-betadine foams, and cellulose sponge material. The synthetic foams should be soft and flexible, open celled, and of medium cell size. Its interior surfaces should be hydrophilic. Incorporation of surfactant during foam manufacture or addition of surfactant to the preformed foam are two suitable methods of insuring that the interior surfaces are hydrophilic. The foam should have a density of from about 0.1 to about 0.8 grams per cubic centimeter.

The acquisition channel 30 is the void space positioned directly beneath the topsheet 22. The acquisition channel 30 provides improved rates of liquid acquisition because no interference to liquid flow is presented directly below the top sheet. 22. Therefore, gushes of liquids will readily and easily pass through the topsheet 22 into the acquisition channel 30 without having an opportunity to flow along the surface of the topsheet 22 creating a danger of leakage. In addition, the acquisition channel 30 provides improved topsheet dryness by not holding liquids near the topsheet 22. Thus there is a reduced likelihood that liquid will be squeezed out of the absorbent core 26 and back through the topsheet 22 causing uncomfort and leakage.

In order to achieve the improved properties discussed above, it is preferred that the acquisition channel 30 be positioned between the topsheet 22 and the absorbent core 26. While wicking layers or other materials may be placed between the topsheet 22 and the acquisition channel 30, such an embodiment is not preferred. In addition, any number of materials or elements may be placed between the acquisition channel 30 and the absorbent core 26. Preferably as shown in FIG. 2, the first liquid distribution layer 52 is positioned immediately below the acquisition channel 30. The side walls of the acquisition channel 30 are defined by the resilient shaping members 28. That is, the acquisition channel 30 is longitudinally bounded by the resilient shaping members 28. Bounded being defined as the exterior or limiting lines of the object.) The acquisition channel 30 is preferably longitudinally bounded to present the longest possible channel. While the acquisition channel 30 may be longitudinally bounded by other elements or materials, such an embodiment is not preferred. In addition, it should be understood that the acquisition channel 30 may be bounded along other dimensions by any element or material.

The transverse width of the acquisition channel 30 is critical to the rapid acquisition characteristics of the incontinent pad 20. If the acquisition channel 30 is too small, the incontinent pad 20 will be unable to rapidly collect and contain large gushes of liquids. The acquisition channel 30 should, therefore, have a transverse width of at least about one-sixth of the total transverse width of the incontinent pad 20. More preferably, the transverse width of the acquisition channel 30 should be at least about one-half, and most preferably two-thirds, of the total transverse width of the incontinent pad 20. Because the incontinent pad 20 shown in FIG. 1 has a preferably transverse width of about 7.6 cm (3 inches), the transverse width of the acquisition channel 30 should be at least about 1.27 cm (0.5 inches).

The liquid distribution layers 52, 54 and 55 serve to quickly collect and temporarily hold discharged body liquids. Since such liquids are discharged in gushes, the liquid distributiton layers must be able to quickly acquire and transport liquids from the point of initial liquid contact to other parts of the liquid distribution layer. The liquid distribution layers also preferably provide a resilient, form retaining member within the interior of the incontinent pad 20. The liquid distribution layers also allow liquid contact with large surface areas of the absorbent core 26.

The liquid distribution layers can be disposed in several locations within the incontinent pad 20. Preferably, however, the liquid distribution layers are disposed on the absorbent core layers. Thus, a first liquid distribution layer 52 is preferably disposed between the resilient shaping members 28 and the first side margin layers 40. A second liquid distribution layer 54 is disposed between the second side margin layers 44 and the first support layers 38. A third liquid distribution layer 55 is disposed between the second support layers 42 and the base layer 36. While the liquid distribution layers are preferably disposed as shown in FIG. 2, the liquid distribution layers may be disposed in different locations, one or more of the liquid distribution layers may be omitted from the structure, or they all may be omitted entirely.

Various types of materials can be used in the liquid distribution layers of the incontinent pad 20. Specific examples of such materials include cellulose fibers, rayon and polyester fibers. Because the liquid distribution layers are preferably resilient and moisture insensitive, it is preferable that the liquid distribution layers be a resilient, low bulk density material. Even more preferably, the liquid distribution layers are the same material as used in the resilient shaping members 28.

As indicated, the primary function of the liquid distribution layers are to receive liquids passing through the relatively hydrophobic, liquid pervious topsheet 22 and to transport such liquids to other areas of the liquid distribution layers and eventually to the absorbent core 26. The liquid distribution layers can thus be substantially free of hydrogel material. Alternatively, the liquid distribution layers can contain small amounts of hydrogel material in particle form as hereinafter described. In some instances, the presence of hydrogel particles in the liquid distribution layers can actually serve to maintain the density of the layer within the optimum range to promote liquid ditribution. The specific type of hydrogel optionally used in the liquid acquisition layers does not have to be the same as the hydrogel type essentially employed in the absorbent core 26.

Since asorbent cores, particularly those which contain hydrogel materials, absorb liquid slowly and expand upon absorption, the incontinent pad 20 preferably has a void space for rapid acquisition and temporary storage of liquids. This void space is generally defined as the liquid acquisition zone 50. The cubic volume defined by the liquid acquisition zone 50 must be at least as large as the liquid volume the product is expected to hold. Expected liquid volumes which will be received by the incontinent pad 20 varies according to the user. Thus, a load of from about 0 to about 300 milliletrs can be expected. Thus, the liquid acquisition zone 50 should have a volume of at least about 30 cm$^3$ and more preferably of from about 65 cm$^3$ to about 300 cm$^3$. As shown in FIG. 2, the incontinent pad 20 preferably has a liquid acquisition zone 50 volume of about 205 cm$^3$.

The liquid acquisition zone 50 comprises the void space available within the product to accept, contain and store rapidly discharged liquid. Therefore, the liquid acquisition zone 50 will comprise the acquisition channel 30, the first central channel 46 and the second central channel 48. In addition, because the liquid distribution layers, and the resilient shaping members 28 preferably have large interstices which can accept and contain liquids, the liquid acquisition zone 50 additionally comprises these elements.

FIGS. 1 and 2 also show the liquid impervious shelves 58 and 60 of the present invention. Each of the sets of shelves channel the flow of the liquid toward the lower layers of the absorbent core 26 and particularly the base layer 36. In addition, the shelves encourage use of the bottom of the side margin layers, thereby resulting in a more efficient use of hydrogel materials. As liquids are acquired in the liquid acquisition zone 50, some of the liquid flows to the sides of the pad. This liquid will contact the liquid impervious shelves and be directed toward the bottom of the side margin layers. Thus the incontinent pad 20 has improved liquid handling through controlled liquid migration.

In order for free liquids to distribute throughout the lower layers of the incontinent pad 20, the shelves must have a maximum transverse width so that the shelves do not present a mechanical barrier to the flow of liquids to the lower layers. The maximum transverse width of each shelf should, therefore, be about five-twelfths of the total maximum transverse width of the incontinent pad 20, or preferably about one-eighth of the total transverse width of the pad. The most preferred arrangement is for each liquid impervious shelf to have a width of about one-fourth of the total transverse width of the incontinent pad 20.

While the liquid impervious shelves may each comprise a separate liquid impervious layer, each of the shelves are preferably formed from a portion of the backsheet arranged in a multiplicity of shelf layers, the shelf layers being formed by longitudinally extending folds in the backsheet. As is shown in FIG. 2, each liquid impervious shelf comprises at least a first shelf layer 62 and a second shelf layer 64.

In the preferred embodiment of the incontinent pad 20 as shown in FIG. 2, the incontinent pad 20 has at least two first liquid impervious shelves 58 and at least two second liquid impervious shelves 60. The first liquid impervious shelves 58 are disposed one on each side of the incontinent pad 20 in a spaced relation to each other between the second side margin layers 44 and the first side margin 40 layers. Preferably, they are positioned between the first support layers 38 and the first side margin layers 40. The second liquid impervious shelves 60 are disposed one on each side of the incontinent pad 20 in a spaced relation to each other between the base layer 36 and the second side margin layers 44. Preferably, the second liquid impervious shelves 60 are disposed between the second support layers 42 and the second side margin layers 44.

While the liquid impervious shelves may be manufactured from any liquid impervious material as is known in the art, the liquid impervious shelves are preferably formed of the same material as the backsheet such as a thin plastic film such as polyethylene.

As shown in FIG. 2, an anti-bunching bead 66 is provided on the incontinent pad 20. The anti-bunching bead 66 secures the first shelf layer 62 of the liquid impervious shelves to the second shelf layer 64 to provide stability for the product so that as the product conforms to the body of the wearer during use, the sides of the pad will not significantly distort into a configuration whereby the resilient shaping members 28 will be squeezed closely together thereby effectively blocking the acquisition channel 30 from the flow of liquids. As shown in FIG. 2, an anti-bunching bead 66 is preferaby positioned on each first liquid impervious shelf 58 and each second liquid impervious shelf 60. While this configuration is preferred, the anti-bunching bead 66 may alternatively not be positioned on any or all of the liquid impervious shelves. Additionally, the anti-bunching bead 66 may extend the entire length of the liquid impervious shelf or it may preferably extend only a fraction of the length of the shelf. The anti-bunching bead 66 may be manufactured from double-sided adhesive tape, hot melt adhesives, hot melt polypropylenes or polyethylenes or any other means as are well known in the art.

The incontinent pad 20 is provided with optional adhesive attachment means 32 as is illustrated in FIG. 2. The adhesive attachment means 32 is illustrated as a wide strip of adhesive positioned on the backsheet 24 and running almost the entire length of the incontinent pad 20. This arrangement is selected for convenience; those skilled in the art can readily select a different pattern for the adhesive attachment means 32.

The purpose of the adhesive attachment means 32 is to secure the incontinent pad 20 in the crotch region of the wearer's undergarment. Any adhesive or glue used with sanitary napkins for such a purpose can be used with this invention. Pressure sensitive adhesives are preferred. Suitable adhesives include Century A-305IV manufactured by Century Adhesive Corporation and Instant Lok 34-2823 manufactured by National Starch Company. Other means for physically securing the incontinent pad 20 in the crotch region of the wearer's undergarment can be used, but adhesive attachment means 32 are preferred.

When adhesive attachment means 32 is present in the device, it is usually covered, prior to the time the wearer affixes the incontinent pad 20 to the undergarment, with a release liner 34. The release liner 34 serves to keep the adhesive attachment means 32 from drying out and from sticking to extraneous surfaces prior to use. Any release liner 34 commonly used for such purposes with sanitary napkins can be used with this invention. Examples of suitable release liners 34 are BL30 MG-A SILOX E1-0 and BL30 MG-A SILOX 4P/O manufactured by Akrosil Corporation.

Referring to FIG. 1, the topsheet 22 and the backsheet 24 are secured to each other at the ends of the incontinent pad 20 with a seal 56. The seal 56 can be achieved by mechanical crimping, thermal welding, ultrasonic welding, adhesive bonding, etc. Although preferably each of the above elements are secured by the seal 56, several alternative embodiments are possible whereby additional elements are secured to the these elements by the seal 56.

In use of the incontinent pad 20 is secured on the inside of the crotch portion of a garment with the adhesive side toward the crotch. The release liner 34 is removed from the incontinent pad 20 to expose the adhesive attachment means 32. The incontinent pad 20 is secured in position by pressing the adhesive attachment means 32 firmly against the crotch material.

FIG. 3 shows an alternative embodiment of the present invention in which the overwrap 21' consists of the topsheet 22 that extends around the entire incontinent pad 20. While the topsheet 22 preferably overwraps the entire structure of the incontinent pad 20, other embodiments are possible whereby the overwrap 21 or the topsheet 22 extends only around the sides and the top of the incontinent pad 20. Because the absorbent core 26 will expand when wetted, the incontinent pad 20 is additionally provided with expansion means 72 for permitting expansion of the topsheet 22 as the absorbent core 26 expands.

The expansion means 72 are any means that would release the topsheet 22 when a slight shearing or peeling action is applied to the expansion means 72. Without the expansion means 72, the expansion of the absorbent core 26 would severely deform the shape of the incontinent pad 20 causing an increase in discomfort and a decrease in its liquid acquisition properties. Thus the expansion means 72 prevents the acquisition channel 30 from becoming so pinched by the absorbent core 26 that the distance between the topsheet 22 and the absorbent core 26 would not be maintained thereby resulting in a loss of the rapid acquisition characteristics of the incontinent pad 20. The expansion means 72 also prevents the absorbent core 26 from being squeezed as it expands so that the danger of rewet is decreased. Examples of such expansion means 72 includes double-sided adhesive tape, mechanical means such as thread or wire, or mechanical fasteners. In a preferred embodiment, as is shown in FIG. 3, the expansion means 72 comprises a releasable tack 74. The releasable tack 74 is an adhesive or glue that has the requisite properties of releasing the topsheet 22 when a slight shearing or peeling force is applied to the releasable tack 74. A particularly preferred releasable tack 74 is hot melt adhesive, although other adhesives as are known in the art are also materials useful as the releasable tack.

The expansion means 72 may be positioned on the incontinent pad 20 in a number of different positions. As is shown in FIG. 3, the releasable tack 74 is positioned on the backsheet 24 so that a portion of the topsheet 22 is secured to backsheet 24 preferably between the second support layer 42 and the second side margin layer 44. However, the topsheet 22 may be additionally or alternatively tacked between the first support layer 38 and the first side margin layers 40 or at any other location along the backsheet 24.

An alternative expansion means is a multiplicity of overwrap layers formed in each side of the incontinent pad 20, the overwrap layers being formed by longitudinally extending folds in the topsheet 22. While a multiplicity of overwrap layers are preferably located on each of the sides of the incontinent pad 20, embodiments are contemplated wherein the multiplicity of layers are formed in only one location on the incontinent pad 20. Thus as the absorbent core expands, the topsheet will expand unfolding the overwrap layers. In this embodiment, the expansion means 72 are positioned on the topsheet 22. The expansion means 72 may additionally comprise a releasable tack positioned between the overwrap layers of the topsheet 22 to releasably secure the overwrap layers together. In this embodiment, the overwrap layers of the topsheet 22 are preferably inward longitudinally extending folds positioned between the core layers of the absorbent core 26, preferably between the support layers and the side margin layers. Alternatively, the overwrap layers may be positioned between the base layer and the side margin layers or between any other core layers of the absorbent core 26 as are configured. In addition, the overwrap layers may be positioned anywhere on the perimeter of the incontinent pad 20 including, for example, along the bottom of the incontinent pad 20.

While particular embodiments of the present invention have been illustrated and described, those skilled in the art will recognize that various changes and modifications can be made without departing from the spirit and scope of the invention. It is intended to cover, in the claims, all such modifications that are within the scope of this invention.

What is claimed is:

1. An absorbent article comprising:
    a liquid pervious topsheet;
    a liquid impervious backsheet joined with said topsheet;
    an absorbent core positioned between said topsheet and said backsheet;
    at least two resilient shaping members disposed one in each longitudinal side of the absorbent article in a longitudinally spaced relation to each other between said absorbent core and said topsheet, said resilient shaping members being moisture insensitive;
    an acquisition channel positioned between said topsheet and said absorbent core, and longitudinally bounded by and coplanar with at least said resilient shaping members; and
    a liquid acquisition zone having a volume of at least 30 cm$^3$, said liquid acquisition zone comprising at least said resilient shaping members and said acquisition channel.

2. The absorbent article of claim 1 wherein each of said resilient shaping members is formed from a resilient material that will recover at least about 80% of its original volume after it is compressed to about 20% of its original volume.

3. The absorbent article of claim 2 wherein each of said resilient shaping members is a batt of compressible, conformable, resilient fibers.

4. The absorbent article of claim 3 wherein the surfaces of said batt of fibers are hydrophilic.

5. The absorbent article of claim 1 wherein each of said resilient shaping members is a synthetic foam.

6. The absorbent article of claim 1 wherein each of said resilient shaping members has a height of at least about 0.5 cm.

7. The absorbent article of claim 1 wherein each of said resilient shaping members has a height of at least about 1.0 cm.

8. The absorbent article of claim 1 wherein the transverse width of said acquisition channel is at least about one-sixth of the total transverse width of the absorbent article.

9. The absorbent article of claim 1 wherein the transverse width of said acquisition channel is at least about one-half of the total transverse width of the absorbent article.

10. The absorbent article of claim 1 wherein the transverse width of said acquisition channel is at least about two-thirds of the total transverse width of the absorbent article.

11. The absorbent article of claim 10 wherein each of said resilient shaping members has a height of at least about 0.5 cm.

12. The absorbent article of claim 11 wherein each of said resilient shaping members is a batt of compressible, conformable, resilient fibers.

13. The absorbent article of claim 12 wherein said absorbent core contains a hydrogel material.

14. An absorbent article comprising:
a liquid pervious topsheet;
a liquid impervious backsheet joined with said topsheet;
an absorbent core positioned between said topsheet and said backsheet, said absorbent core comprising a mixture of fiber material and hydrogel particles and having
(i) a base layer positioned adjacent said backsheet,
(ii) at least two coplanar first side margin layers disposed one in each longitudinal side of the absorbent article in a lonitudinally spaced relation to each other between said base layer and said topsheet, and
(iii) a first central channel positioned between said base layer and said topsheet, and longitudinally bounded by and coplanar with at least said first side margin layers;
at least two resilient shaping members disposed one in each longitudinal side of the absorbent article in a longitudinally spaced relation to each other between said absorbent core and said topsheet, said resilient shaping members being moisture insensitive and having a height of at least about 0.5 cm;
an acquisition channel positioned between said topsheet and said absorbent core, and longitudinally bounded by and coplanar with at least said resilient shaping members, the transverse width of said acquisition channel being at least about one-half of the total transverse width of the absorbent article;
a first liquid distribution layer disposed between said first side margin layers and said resilient shaping members; and
a liquid acquisition zone having a volume of at least 30 cm$^3$, said liquid acquisition zone comprising at least said first liquid distribution layer, said first central channel, said acquisition channel and said resilient shaping members.

15. The absorbent article of claim 14 additionally comprising a second liquid distribution layer disposed between said base layer and said first side margin layers, said liquid acquisition zone additionally comprising said second liquid distribution layer.

16. The absorbent article of claim 15 wherein said absorbent core additionally comprises at least two coplanar second side margin layers disposed one in each longitudinal side of the absorbent article in a longitudinally spaced relation to each other between said base layer and said second distribution layer, and a second central channel positioned between said base layer and said second liquid distribution layer; and longitudinally bounded by and coplanar with at least said second side margin layers, said liquid acquisition zone additionally comprising said second central channel.

17. The absorbent article of claim 16 additionally comprising a third liquid distribution layer disposed between said base layer and said second side margin layers, said liquid acquisition zone additionally comprising said third liquid distribution layer.

18. The absorbent article of claim 17 wherein each of said resilient shaping members is a batt of compressible comformable, resilient fibers.

19. An absorbent article comprising:
a liquid pervious topsheet;
a liquid impervious backsheet joined with said topsheet;
a layered absorbent core superposed on said backsheet, said absorbent core comprising a mixture of fiber material and hydrogel particles and being a unified web arranged in a multiplicity of core layers, said core layers being formed by longitudinally extending folds in said web, the folds alternating in a zig-zag sequence in each longitudinal side of the absorbent article, said core layers comprising:
(i) a base layer positioned adjacent said backsheet,
(ii) at least two coplanar first support layers joined to said base layer and disposed one on each longitudinal side of the absorbent article in a longitudinally spaced relation to each other, and
(iii) at least two coplanar joined to first support layers and first side margin layers disposed one on each longitudinal side of the absorbent article in a longitudinally spaced relation to each other to define a first central channel between said first side margin layers, said first side margin layers being spaced so that said first central channel has a transverse width of at least about one-half of the total transverse width of the absorbent article;
at least two resilient shaping members disposed one in each longitudinal side of the absorbent article in a longitudinally spaced relation to each other between said absorbent core and said topsheet, said resilient shaping members being moisture insensitive and having a height of at least about 0.5 cm;
an acquisition channel positioned between said topsheet and said absorbent core, and longitudinally bounded by and coplanar with at least said resilient shaping members, the transverse width of said acquisition channel being at least about one-half of the total transverse width of the absorbent article; and a liquid acquisition zone having a volume of at least 30 cm$^3$ said liquid acquisition zone comprising at least said resilient shaping members and said acquisition channel.

20. The absorbent article of claim 19 additionally comprising a first liquid distribution layer disposed between said side margin layers and said resilient shaping members.

21. The absorbent article of claim 20 additionally comprising a second liquid distribution layer disposed between said base layer and said first side margin layers, said liquid acquisition zone additionally comprising said second liquid distribution layer.

22. The absorbent article of claim 21 wherein said absorbent core additionally comprises:
(iv) at least two coplanar second support layers joined to said first side margin layers and disposed one on each longitudinal side of the absorbent article in a longitudinally spaced relation to each other, and
(v) at least two coplanar second side margin layers joined to said second support layers and one on each longitudinal side of the absorbent article in a longitudinally spaced relation to each other to define a second central channel between said second side margin layers, said second side margin layers being spaced so that said second central channel has a transverse width of at least about one-half of the total transverse width of the absorbent article.

23. The absorbent article of claim 22 additionally comprising a third liquid distribution layer disposed between said second support layer and said first side margin layers, said liquid acquisition zone additionally comprising said third liquid distribution layer.

24. The absorbent article of claim 23 wherein each of said resilient shaping members has a height of at least about 1.0 cm, and wherein the transverse width of said acquisition channel is at least about two-thirds of the total transverse width of the absorbent article.

25. The absorbent article of claim 24 wherein said resilient shaping members are inwardly rolled so as to be wider in the midle than at the top and at the bottom.

26. The absorbent article of claim 25 wherein said resilient shaping members are integrally formed with said first liquid distribution layer.

27. An incontinent pad comprising:
an overwrap which extends around the entire incontinent pad comprising a liquid pervious topsheet and a liquid impervious backsheet joined with said topsheet;
a layered absorbent core positioned between said topsheet and said backsheet, said absorbent core comprising a mixture of fiber material and hydrogel particles and having
  (i) a base layer positioned adjacent said backsheet, and
  (ii) two coplanar side margin layers disposed between said base layer and said topsheet, one of said side margin layers being positioned in each longitudinal side of the incontinent pad in a longitudinally spaced relation to each other to define a central channel between said side margin layers, said side margin layers being spaced so that said central channel has a width of at least about one-half of the total transverse width of the incontinent pad;
an adhesive attachment means positioned on said backsheet;
a release liner covering said adhesive attachment means;
at least two resilient shaping members disposed one in each longitudinal side of the absorbent article in a longitudinally spaced relation to each other between said absorbent core and said topsheet, said resilient shaping members being moisture insensitive and having a height of at least about 0.5 cm;
an acquisition channel positioned between said topsheet and said absorbent core, and longitudinally bounded by and coplanar with at least said resilient shaping members, the transverse width of said acquisition channel being at least about one-half of the total transverse width of the incontinent pad; and
a liquid acquisition zone having a volume of at least 30 cm$^3$, said liquid acquisition zone comprising at least said resilient shaping members and said acquisition channel.

28. The incontinent pad of claim 27 wherein each of said resilient shaping members has a height of at least about 1.0 cm, and wherein the transverse width of said acquisition channel is at least about two-thirds of the total transverse width of the incontinent pad.

* * * * *

UNITED STATES PATENT AND TRADEMARK OFFICE
CERTIFICATE OF CORRECTION

PATENT NO. : 4,781,711

DATED : November 1, 1988

INVENTOR(S) : Dawn I. Houghton et al.

It is certified that error appears in the above-identified patent and that said Letters Patent is hereby corrected as shown below:

| | |
|---|---|
| Column 1, Line 35, | "with" should read ---within---. |
| Column 2, Line 16, | "absorbent material would" should read ---absorbent capacity. It would---. |
| Column 4, Line 10, | "gen" should read ---gel---. |
| Column 4, Line 56, | ""incontinent persons"" should read ---incontinent pad" refers to a garment generally worn by incontinent persons---. |
| Column 9, Line 59, | "layes" should read ---layers---. |
| Column 10, Line 3, | "available this" should read ---available, this---. |
| Column 11, Line 34, | "arranted" should read ---arranged---. |
| Column 11, Line 39, | "resilinet." should read ---resilient.---. |
| Column 11, Line 64, | "parking" should read ---packing---. |
| Column 12, Line 14, | "aninherent" should read ---an inherent---. |
| Column 14, Line 13, | "exterior" should read ---external---. |
| Column 14, Line 34, | "preferably" should read ---preferable---. |

UNITED STATES PATENT AND TRADEMARK OFFICE
CERTIFICATE OF CORRECTION

PATENT NO. : 4,781,711

DATED : November 1, 1988

INVENTOR(S) : Dawn I. Houghton et al.

It is certified that error appears in the above-identified patent and that said Letters Patent is hereby corrected as shown below:

Column 14, Line 40, "distributiton" should read ---distribution---.

Column 19, Line 50, "lonitudinally" should read ---longitudinally---.

Column 20, Line 31, "compressible comformable" should read ---compressible, comformable---.

Column 20, Line 50, "coplanar joined to first support layers and first side margins layers disposed" should read ---coplanar first side margin layers joined to said first support layers and disposed---.

Signed and Sealed this

Twenty-fifth Day of July, 1989

Attest:

DONALD J. QUIGG

Attesting Officer

Commissioner of Patents and Trademarks